United States Patent
Hammon et al.

(10) Patent No.: US 9,643,910 B2
(45) Date of Patent: May 9, 2017

(54) EXTRACTION COLUMN AND PROCESS FOR EXTRACTING A CONSTITUENT FROM A FLUID

(71) Applicant: BASF SE, Ludwigshafen (DE)

(72) Inventors: Ulrich Hammon, Mannheim (DE); Daniel Pfeiffer, Neustadt (DE); Jonathan Walter, Eppelheim (DE)

(73) Assignee: BASF SE, Ludwigshafen (DE)

( * ) Notice: Subject to any disclaimer, the term of this patent is extended or adjusted under 35 U.S.C. 154(b) by 13 days.

(21) Appl. No.: 14/573,313

(22) Filed: Dec. 17, 2014

(65) Prior Publication Data

US 2015/0166455 A1 Jun. 18, 2015

Related U.S. Application Data

(60) Provisional application No. 61/917,368, filed on Dec. 18, 2013.

(30) Foreign Application Priority Data

Dec. 18, 2013 (DE) .................. 10 2013 226 428

(51) Int. Cl.
*B01D 3/40* (2006.01)
*C07C 51/48* (2006.01)
(Continued)

(52) U.S. Cl.
CPC .............. *C07C 51/48* (2013.01); *B01D 3/141* (2013.01); *B01D 3/40* (2013.01); *B01D 11/043* (2013.01);
(Continued)

(58) Field of Classification Search
CPC .............................. B01D 11/0426; B01D 3/40
(Continued)

(56) References Cited

U.S. PATENT DOCUMENTS 5,758,819 A 6/1998 Sniegocki
6,498,272 B1 12/2002 Schröder et al.
(Continued)

FOREIGN PATENT DOCUMENTS

DE 1 794 020 10/1971
DE 198 38 845 A1 3/2000
(Continued)

OTHER PUBLICATIONS

U.S. Appl. No. 14/737,025, filed Jun. 11, 2015, Hammon, et al.
(Continued)

*Primary Examiner* — Kamal Saeed
*Assistant Examiner* — Janet L Coppins
(74) *Attorney, Agent, or Firm* — Oblon, McClelland, Maier & Neustadt, L.L.P.

(57) ABSTRACT

The present invention relates to an extraction column 1 having a vertically aligned column body 2 which is cylindrical at least in sections and forms a column cavity 3 having a horizontal maximum extent, with provision in the column body 2 of at least one first feed 4 for an extractant, at least one second feed 5 for the fluid to be extracted and at least one outlet 6 for the extract mixture and at least one outlet for the raffinate. In the inventive extraction column 1, a vertically aligned divider 7 arranged within the column cavity 3 subdivides the column cavity 3 into a plurality of vertically aligned and horizontally divided regions, the horizontal maximum extent of each region being less than the horizontal maximum extent of the column cavity 3. The invention further relates to a process for extracting a constituent from a fluid by means of such an extraction column 1.

26 Claims, 6 Drawing Sheets

Figure 1:
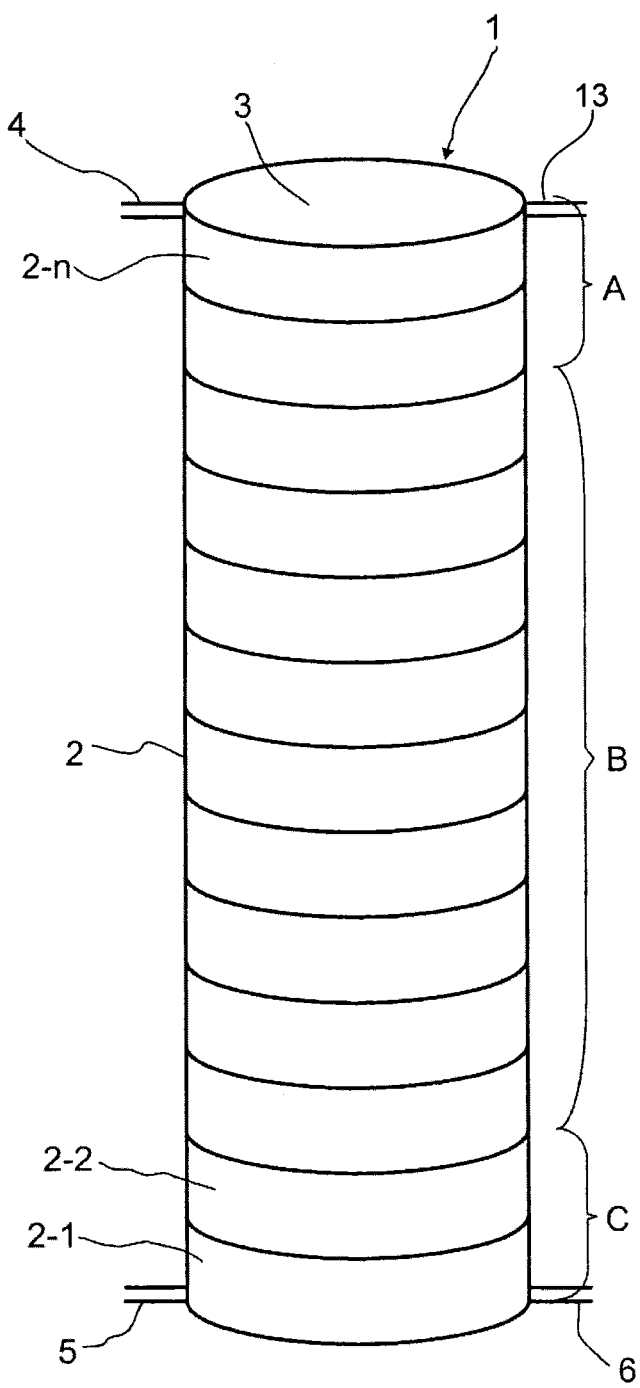

(51) Int. Cl.
*B01D 11/04* (2006.01)
*B01D 3/14* (2006.01)
*B01D 11/00* (2006.01)

(52) U.S. Cl.
CPC .... *B01D 11/0426* (2013.01); *B01D 2011/002* (2013.01)

(58) Field of Classification Search
USPC .............................. 202/152, 153, 168, 169
See application file for complete search history.

(56) References Cited

U.S. PATENT DOCUMENTS

| | | | |
|---|---|---|---|
| 6,679,939 B1 | 1/2004 | Thiel et al. | |
| 7,169,213 B2 * | 1/2007 | Liu | B01D 46/0021 210/490 |
| 2003/0060661 A1 | 3/2003 | Eck et al. | |
| 2004/0073063 A1 | 4/2004 | Thiel et al. | |
| 2004/0097756 A1 | 5/2004 | Thiel et al. | |
| 2004/0256319 A1 | 12/2004 | Hammon et al. | |
| 2005/0006299 A1 | 1/2005 | Heilek et al. | |
| 2005/0090628 A1 | 4/2005 | Eck et al. | |
| 2006/0199977 A1 | 9/2006 | Heilek et al. | |
| 2008/0183013 A1 | 7/2008 | Dubois et al. | |
| 2008/0183014 A1 | 7/2008 | Diefenbacher et al. | |
| 2009/0134357 A1 | 5/2009 | Bub et al. | |
| 2013/0005925 A1 | 1/2013 | Hütten et al. | |
| 2013/0274519 A1 | 10/2013 | Mueller-Engel et al. | |

FOREIGN PATENT DOCUMENTS

| | | |
|---|---|---|
| DE | 199 24 532 A1 | 11/2000 |
| DE | 199 24 533 A1 | 11/2000 |
| DE | 101 56 016 A1 | 6/2003 |
| DE | 102 35 847 A1 | 8/2003 |
| DE | 102 23 058 A1 | 12/2003 |
| DE | 102 43 625 A1 | 4/2004 |
| DE | 103 32 758 A1 | 5/2004 |
| DE | 10 2005 015 637 A1 | 10/2006 |
| DE | 10 2007 004 960 A1 | 7/2008 |
| DE | 10 2007 055 086 A1 | 5/2009 |
| DE | 10 2012 204 438 A1 | 10/2012 |
| DE | 10 2011 076 931 A | 12/2012 |
| EP | 0 640 367 A1 | 3/1995 |
| EP | 1 710 227 A1 | 10/2006 |
| GB | 1 245 646 | 9/1971 |
| WO | WO 00/53560 A1 | 9/2000 |
| WO | WO 01/77056 A1 | 10/2001 |
| WO | WO 2004/035514 A1 | 4/2004 |
| WO | WO 2006/092272 A2 | 9/2006 |
| WO | WO 2006/114506 A1 | 11/2006 |
| WO | WO 2008/090190 A1 | 7/2008 |

OTHER PUBLICATIONS

W. Meier, et al. ,"Sulzer-Kolonnen for Rektifikation and Absorption", Technische Rundschau Sulzer Feb. 1979, pp. 49-61.
Alfons Mersmann, et al. ,"Packungskolonnen", Chem.-Ing. -Tech., vol. 58, No. 1, (1986), pp. 19-31 (with English abstract).
Norbert Asprion, et al., "Dividing wall columns: Fundamentals and recents advances", Chemical Engineering and Processing: Process Intensification, vol. 49, (2010), pp. 139-146.

* cited by examiner

EXTRACTION COLUMN AND PROCESS FOR EXTRACTING A CONSTITUENT FROM A FLUID

The present invention relates to an extraction column having a vertically aligned column body which is cylindrical at least in sections and forms a column cavity having a horizontal maximum extent. In the column body, at least one first feed for an extractant, at least one second feed for the fluid to be extracted and at least one outlet each for the laden extractant and the raffinate have been provided. The invention further relates to a process for extracting a constituent from a fluid by means of an extraction column having a cylindrical, vertically aligned column body which forms a column cavity having a horizontal maximum extent.

Extraction involves separating a component, which is also referred to as transfer component or extract, from a substance mixture, which is also referred to as extraction mixture or substance to be extracted, with the aid of an extractant. Extraction does not fully separate the components of the extraction mixture. Instead, the extract is transferred to the extractant and is obtained as an extract mixture. The extraction mixture remains as raffinate comprising a lower level of extract.

The present invention relates more particularly to solvent extraction, in which a dissolved extract is separated from liquid extraction mixtures by means of selective liquid extractants.

Such an extraction is used, for example, in the preparation of acrylic acid. Acrylic acid is an important intermediate which finds use, for example, in the preparation of polymer dispersions (optionally also in the form of esters thereof with alkanols) and of water-superabsorbent polymers.

One way in which acrylic acid is obtainable is by heterogeneously catalyzed gas phase partial oxidation of $C_3$ precursors (of $C_3$ precursor compounds) of acrylic acid (this term shall especially encompass those chemical compounds obtainable in a formal sense by reduction of acrylic acid; known $C_3$ precursors of acrylic acid are, for example, propane, propene, acrolein, propionaldehyde and propionic acid; the term shall also encompass precursor compounds of the aforementioned compounds, for example glycerol (proceeding from glycerol, acrylic acid can be obtained, for example, by heterogeneously catalyzed oxidative dehydration in the gas phase; cf., for example, EP-A 1 710 227, WO 06/114506 and WO 06/092272)) with molecular oxygen over solid-state catalysts at elevated temperature.

This involves passing the starting gases mentioned, generally diluted with inert gases, for example nitrogen, $CO_2$, saturated hydrocarbons and/or steam, in a mixture with molecular oxygen, over mixed oxide catalysts (for example mixed transition metal oxide catalysts) at elevated temperatures and optionally elevated pressure, and converting them oxidatively to a product gas mixture comprising acrylic acid, water and unwanted by-products, for example furfurals, benzaldehyde, acetone, formaldehyde and maleic anhydride etc., from which the acrylic acid has to be separated (the by-products and the inert diluent gases other than steam are to be referred to collectively in this document by the term "secondary components"; in addition, this term shall include the polymerization inhibitors typically added in the acrylic acid separation processes).

Proceeding from propionaldehyde and/or propionic acid, the heterogeneously catalyzed gas phase partial oxidation with molecular oxygen is at least partly an oxidative dehydrogenation.

Documents DE-A 199 24 533, DE-A 199 24 532, WO 01/77056, DE-A 101 56 016, DE-A 102 43 625, DE-A 102 23 058, DE-A 102 35 847, WO 2004/035514, WO 00/53560 and DE-A 103 32 758 disclose processes as described at the outset for preparation of acrylic acid, in which a basic removal of a crude acrylic acid is undertaken by fractional condensation of the product gas mixture of the heterogeneously catalyzed gas phase partial oxidation. The term "crude acrylic acid" expresses the fact that the acrylic acid withdrawn via the first side draw is not a pure product but a mixture which, as well as acrylic acid (generally ≥50 or ≥60% by weight, usually ≥70 or ≥80% by weight, in many cases ≥90% by weight and frequently ≥95% by weight or more of the total weight), also comprises water and secondary components, for example lower aldehydes (e.g. furfurals, acrolein, benzaldehyde), lower carboxylic acids (e.g. acetic acid, propionic acid, formic acid) etc. In any case, the total content of water and secondary components, based on the content of acrylic acid, is lower in the crude acrylic acid than in the product gas mixture of the gas phase partial oxidation, and for that reason it is also stated that the crude acrylic acid comprises these constituents in depleted form overall (individual constituents, in contrast, may be present in comparatively enriched form in the crude acrylic acid).

In some cases, the purity of the crude acrylic acid thus separated is already sufficient for the contemplated end use of the acrylic acid (for example for the purpose of esterification thereof, or for the purpose of formation of polymers obtainable by free-radical polymerization). In many cases, the crude acrylic acid separated will, however, be subjected to at least one further thermal separation process, in order to obtain, from the crude acrylic acid, a purer acrylic acid (having a higher acrylic acid content in percent by weight compared to the crude acrylic acid) which has the purity required for the particular end use.

Thermal separation processes are understood to mean those in which a physically at least biphasic system is obtained with supply of or with removal of (generally thermal) energy, the temperature and mass gradients which exist between the phases resulting in heat and mass transfer, which ultimately causes the desired separation, and extraction.

Frequently, thermal separation processes are performed in separation columns comprising separating internals, in which the aforementioned at least two physical phases are generally conducted in countercurrent to one another. In many cases, one of the two physical phases is gaseous (it is generally conducted as the ascending phase in a separation column) and the other is liquid (it is generally conducted as the descending phase in a separation column). In principle, the at least two physical phases may also be liquid (for example in the case of an extraction) or solid and liquid (for example in the case of a crystallization), or solid and gaseous (for example in the case of an adsorption).

Examples of configurations of thermal separation processes in which one of the at least two physical phases is liquid and one is gaseous, and hence a natural element of the term "thermal separation process" used in this document, are rectification (an ascending vapor phase is conducted in countercurrent to a descending liquid phase in the separation column) and desorption (the converse process of absorption; the gas dissolved in a liquid phase is removed from the liquid phase by lowering the pressure above the liquid phase, by increasing the temperature of the liquid phase and/or by passing a gas phase through the liquid phase; if this involves passing a gas phase through, the desorption is also referred to as stripping). Absorption (in general, a gas ascending within a separation column is conducted in countercurrent to at least one absorbent descending in liquid form in the separation column) and fractional condensation of a gas mixture (gas/liquid phase example) also form part of the term "thermal separation process". A particularly favorable thermal separation process for further purification of crude acrylic acid is crystallizative further purification (crystallization).

However, a disadvantage of the known processes for basic removal of a crude acrylic acid by fractional condensation of the product gas mixture of a heterogeneously catalyzed gas phase partial oxidation of at least one $C_3$ precursor of acrylic acid is the additional occurrence of acidic water still comprising acrylic acid and secondary components (also referred to in simplified form as "acid water"). This term "acid water" first of all expresses the fact that the acid water generally comprises $\geq 50\%$ by weight, frequently $\geq 60\%$ by weight, in many cases $\geq 70\%$ by weight and often $\geq 80\%$ by weight of water (this is generally both water of reaction and dilution water (steam) also used as inert diluent gas in the course of the gas phase partial oxidation).

This term also expresses the fact that it comprises, as well as water, secondary component acids, for example propionic acid, acetic acid and formic acid, and also acrylic acid, and hence has a pH of <7 (the total content of secondary component carboxylic acids other than acrylic acid is generally, based on the weight of the acid water, at values of $\leq 10\%$ by weight, in some cases at values of $\leq 5\%$ by weight).

Normally, the acrylic acid content of the acid water will be 4% or 5% to 15%, frequently about 10%, by weight. A disadvantage of the processes recommended in the cited prior art for basic removal of acrylic acid from the product gas mixture of the heterogeneously catalyzed gas phase partial oxidation is that they send the entirety of the acid water which still comprises acrylic acid and is not recycled into the rectification column to incineration (cf. especially DE-A 102 43 625, WO 2004/035514 and DE-A 103 32 758). This is disadvantageous in that the acid water incineration reduces, for example, the yield of the desired acrylic acid product.

DE 10 2007 055 086 A1 or WO 2008/090190 A1 therefore proposes a process for preparing acrylic acid in which an elevated yield of acrylic acid is ensured by extracting acrylic acid from the acid water and recycling it.

DE 10 2007 055 086 A1 accordingly describes a process for preparing acrylic acid, in which a product gas mixture comprising acrylic acid, steam and secondary components is obtained by heterogeneously catalyzed gas phase partial oxidation of at least one $C_3$ precursor (a $C_3$ precursor compound) of acrylic acid with molecular oxygen over solid-state catalysts at elevated temperature. The temperature of the product gas mixture comprising acrylic acid, steam and secondary components is optionally reduced by direct cooling (by direct contact with a cooling liquid) and/or indirect cooling. The product gas mixture comprising acrylic acid, steam and secondary components is then passed into a condensation column equipped with separating elements. The product gas mixture then ascends into itself within the condensation column and is fractionally condensed. A crude acrylic acid comprising water and secondary components depleted overall is conducted out of the condensation column as the target product via a first side draw disposed above the feed point of the product gas mixture into the condensation column. Acidic water (acid water) still comprising acrylic acid and secondary components is conducted out of the condensation column via a second liquid phase draw disposed above the first side draw (preferably a side draw; all statements in this document are valid especially in the case of such an acid water side draw). A residual gas mixture comprising secondary components having lower boiling points (boiling at a lower temperature (based on atmospheric pressure)) than water is conducted out of the condensation column at the top of the condensation column, and a bottoms liquid still comprising acrylic acid and conversion products and secondary components having higher boiling points than acrylic acid from the bottom space of the condensation column. A portion of the acidic water withdrawn is recycled as such and/or after cooling thereof as reflux liquid into the condensation column. The crude acrylic acid is optionally subjected to at least one further thermal separation process for the purpose of its further purification. In the process, acrylic acid present at least in a portion of acidic water not recycled into the condensation column is taken up from the acidic water into an organic solvent by extraction with the organic solvent to form an organic extract comprising acrylic acid. Subsequently, the acrylic acid is removed from the organic extract using at least one thermal separation process and acrylic acid removed from the extract is recycled into the condensation column or sent to the further purification of the crude acrylic acid and/or taken up into the aqueous solution of a metal hydroxide.

The internal diameter of the extraction column specified in DE 10 2007 055 086 A1 is 800 mm. In order to be able to process greater amounts of acid water, there is a need also to use larger extraction columns, which especially have a greater internal diameter. It has been found that the yield of recovery of acrylic acid from the acid water worsens when the internal diameter of the extraction column becomes too great. It has therefore been proposed that greater amounts of acid water be processed by means of thinner extraction columns connected in parallel. However, this is disadvantageous for reasons of cost.

It was accordingly an object of the present invention to provide an extraction column which has been improved in terms of axial backmixing, and an improved process for extracting a constituent from a fluid by means of an extraction column, which has the particular feature of ensuring an elevated yield of the constituent in the extraction even when the extraction column has a large diameter.

This object is achieved in accordance with the invention by an extraction column having the features of claim 1, and by a process having the features of claim 12.

Advantageous configurations and developments are apparent from the dependent claims.

Accordingly, an extraction column having a vertically aligned column body which is cylindrical at least in sections and forms a column cavity having a horizontal maximum extent has been found. In the column body, at least one first feed for an extractant, at least one second feed for the fluid to be extracted and at least one outlet for the extract mixture and at least one outlet for the raffinate have been provided. It is a characteristic feature of the inventive extraction column that a vertically aligned divider arranged within the column cavity subdivides the column cavity into a plurality of vertically aligned and horizontally divided regions. The horizontal maximum extent of each region is less than the horizontal maximum extent of the column cavity.

In this document, the horizontal maximum extent is understood to mean the greatest distance between any two points on the inner surface of the column body or the surface of the dividing wall in a particular horizontal plane through the column body. For clarity, it should be noted that the connecting line between these any two points need not be completely within the region for which the horizontal maximum extent is ascertained. It may also cross another region. Thus, in the case of a circular cylindrical column body, the horizontal maximum extent of the column body is the internal diameter of the column body. When the column cavity is subdivided by the divider, the horizontal maximum extent of a region formed by the divider is the greatest distance between any two points on the inner surface of the column body and/or the surface of the dividing wall, each of which bounds the region, in a particular horizontal plane.

In this document, a divider is understood to mean a device which prevents crossflow, i.e. flow in a horizontal plane from one region into the other region. Thus, there is no horizontal mass transfer from one region to the other region in the extraction column. Crossflow for mass transfer can take place only within one region. Of course, there is additionally mass transfer in the vertical direction.

It is assumed that the worsening of the extract yield in the case of extraction with extraction columns having a relatively high diameter is caused by horizontal crossflow of the fluid to be extracted. It is assumed that this crossflow is caused by axial vortices which form in the case of a relatively large internal diameter of the extraction column. This problem is solved in accordance with the invention by the vertical subdivision of the column cavity by means of the divider. In order to avoid disadvantageous axial vortices, it is important that the divider does not just subdivide the column cavity vertically into separate regions, but that the horizontal maximum extent in the column cavity is also reduced by the divider.

In one configuration of the inventive extraction column, the horizontal maximum extent of each region at each horizontal section through the column body cut by the divider is less than the horizontal maximum extent of the column cavity. The divider extends especially in the vertical direction over a middle section of the column cavity. Above the divider is the column head, and below it is the column bottom. The divider optionally does not extend into the head of the column and into the bottom of the column. If the geometry in the region of the divider is then considered, the divider reduces the horizontal maximum extent in the column cavity at each horizontal section.

The form of the divider depends essentially on the geometry of the horizontal cross section of the column body. Typically, this cross section is circular. The horizontal maximum extent of the column cavity in this case is the internal diameter of the column body. In such a case, halving the column cavity vertically by means of a divider does not lead to a decrease in the horizontal maximum extent in the column cavity. At the side of such a divider, the horizontal maximum extent of the two regions would be equal to the internal diameter of the column body. The slight decrease in the maximum extent that would arise through the wall thickness of the divider is ignored in this case.

According to the invention, the ratio of the greatest horizontal maximum extent of a region to the horizontal maximum extent of the column cavity is less than 0.95, especially less than 0.9 and preferably less than 0.75.

If the column body is circular at a horizontal section, the divider, for example, subdivides the column cavity into at least three vertically aligned and horizontally divided regions. The divider may comprise, for example, three vertical dividing sheets, each of which extends radially from the middle of the column cavity to the column body, more particularly enclosing an angle of 120°.

In addition, the divider can subdivide the column cavity into four vertically aligned and horizontally divided regions. In this case, for example, two dividing sheets arranged crosswise, which enclose an angle of 90°, can subdivide the column cavity into four circle segments of equal size.

In another configuration, the divider forms a central middle region arranged at a distance from the column body. Between the middle region and the column body, at least two further regions are formed. Preferably several further regions are formed between the middle region and the column body. These may, for example, extend radially inward from the column body to the dividing wall which forms the central middle region. In this case, the central middle region may have a circular cross section. This circular cross section is especially concentric with respect to the circular cross section of the column body. However, the cross section of the middle region may also have the shape of a polygon, especially of an equilateral polygon, in which case the radially aligned dividing sheets extend from the corners of the polygon to the column body.

In the described configurations of the divider, the horizontal maximum extent of the column cavity is reduced to a different degree in each case. The mutually divided regions formed by the divider have a significantly lower horizontal maximum extent. The disadvantageous crossflow in the column cavity is thus effectively prevented by the divider.

Preferably, each of the regions formed by the divider are of equal size. This achieves the effect that essentially the same volume of the fluid to be extracted is present in each of the regions.

In addition, the regions formed by the divider at each horizontal section through the column body cut by the divider may have the same geometry. The areas of the regions formed at the horizontal sections are especially identical. This has the advantage that it is possible to use identical packing elements in the regions, as will be explained later. This leads to a reduction in cost in the production of the inventive extraction column.

In a further configuration of the inventive extraction column, the upper ends of the regions open into a common column head, and the lower ends open into a common column bottom. In the region of the column head and the region of the column bottom, the horizontal extent of the column cavity is thus not subdivided by a divider. The regions are thus connected in parallel. One of the feeds and optionally an outlet are arranged in the column head. The other feed and optionally an outlet are arranged in the column bottom.

The inventive extraction column especially has a high diameter. The internal diameter of the column body, i.e. the horizontal maximum extent of the column cavity, is, for example, greater than or equal to 800 mm, especially greater than or equal to 1000 mm. However, column diameters of more than 2000 mm or 5000 mm are also possible.

The height of the column body is, for example, greater than 5 m, especially greater than 10 m. However, it is also possible that the height of the column body exceeds 30 m or 40 m.

Appropriately for application purposes, separating internals are arranged in the column cavity. The separating internals improve mass separation in the extraction column. The internals are provided separately for the regions formed by the divider, meaning that the divider also separates the internals from one another, such that no mass transfer between the regions formed by the divider is possible via the internals either.

The separating internals are specially designed such that the mass transfer between a disperse droplet phase and a continuous phase is improved. The continuous phase is especially not a wetting film phase. The separating internals are specially configured such that they form liquid droplets. In this case, the surface area provided by the liquid droplets is constantly newly formed and renewed by splitting and coalescence. Since the emulsion droplets come into contact and fuse in the course of coalescence, the droplets increase in size, whereas the surface area formed by the disperse phase decreases. The separating internals split the fused droplets back up into smaller droplets, such that the surface area formed by the disperse phase increases again.

The internals may be provided, for example, in the form of packing elements, especially structured or ordered packing elements, tower packing and/or random packings. Among the random packings, preference is given to those comprising rings, helices, saddles, Raschig, Intos or Pall rings, barrel or Intalox saddles, Top-Pak etc. Packing elements particularly suitable for extraction columns to be used in accordance with the invention are, for example, packing elements from Julius Montz GmbH in D-40705 Hilden, for example the Montz-Pak B1-350 packing element. Preference is given to using perforated structured packing elements made from stainless steel sheets. Packed columns having ordered packing elements are known per se to those skilled in the art and are described, for example, in Chem.-Ing. Tech. 58 (1986) no. 1, p. 19-31 and in the Technischen Rundschau Sulzer 2/1979, p. 49 ff. from Gebrüder Sulzer Aktiengesellschaft in Winterthur, Switzerland.

In addition, extraction columns having internals in the form of trays are also suitable, in the case of which a distinction has to be drawn between pulsed sieve tray columns and crossflow sieve tray columns. In the case of pulsed sieve tray columns, the two phases are conducted through the passage orifices (generally holes, i.e. circular passage orifices) in the sieve tray. At the upward stroke in the pulsation, the lighter phase is forced upward through the holes in the sieve tray, and at the downward stroke the heavier phase is correspondingly forced downward. Columns of this kind are described in Pilhofer/Mewes "Siebboden-Extraktionskolonnen: Vorausberechnung unpulsierter Kolonnen" [Sieve Tray Extraction Columns: Predictive Calculation for Unpulsed Columns], Verlag Chemie Weinheim, New York 1979 ISBN 3-527-25837-X. When crossflow sieve tray columns are used, the continuous phase passes from one tray to the next tray through downcomers, and only the disperse phase is forced through the holes of the sieve trays because of the density differential. A further column type is that of extraction columns having moving stirrers, as supplied under the "Kühni column" name by Sulzer.

In a development of the inventive extraction column, the separating internals in the regions formed by the divider are formed from identical individual packing elements. The geometry of a horizontal section through an individual packing element corresponds to the geometry of a horizontal section through the region in which the individual packing element is to be arranged. An individual packing element can therefore be introduced into the region in vertical direction. This reduces the production and assembly costs for the extraction column.

In a development of the inventive extraction column, the divider is subdivided into vertical segments placed one on top of another in the column cavity. The height of the individual packing element may correspond to the height of a vertical segment of the divider. In addition, it is possible that the height of a vertical segment is somewhat greater than or somewhat less than the height of a vertical segment of the divider. These measures simplify the assembly of the extraction column.

In a preferred development of the inventive extraction column, at least one vertically aligned groove in which the divider engages is formed on the inside of the column body. In this way, the divider is positioned so as to prevent rotation in the column cavity. This is advantageous especially when the column body has a circular horizontal cross section.

The formation of a groove on the inside of the column body is preferred over the formation of a projection on the inside of the column body, since a projection would project into a region formed by the divider, and so this projection would have to be cut out in the internals. This would be costly in the production of the internals. In the case of the inventive formation of the inside of the column body with a groove, it is unnecessary to make a cutout in the internals. The internals can thus be produced less expensively.

In a further configuration, several grooves in which dividing sheets of the divider engage are formed on the inside of the column body. For example, all the dividing sheets which extend to the inside of the column body can engage in grooves formed on the inside of the column body.

For the engagement of the divider in a groove or several grooves in the inner wall of the shell, the divider may comprise at least three layers. In this case, the middle layer protrudes with respect to the outer layers. This middle layer then engages in a groove. The ends of the outer layers are then directly adjacent to the inside of the column body, in each case alongside the groove. They especially abut this inside in a fluid-tight manner. This symmetric structure of the divider ensures that the regions formed by the divider have identical cross-sectional areas.

In the process according to the invention for extracting a constituent from a fluid by means of an extraction column having a cylindrical, vertically aligned column body which forms a column cavity having a horizontal maximum extent, the fluid to be extracted is introduced into a plurality of vertically aligned and horizontally divided regions which are formed in the column cavity by a vertically aligned divider which subdivides the column cavity into the regions, the horizontal maximum extent of each region being less than the horizontal maximum extent of the column cavity. In the process, moreover, an extractant is introduced into the regions of the column cavity. The constituent of the fluid to be extracted is then taken up by the extractant in the regions of the column cavity and withdrawn in the form of extract mixture.

In the process according to the invention, the horizontal crossflow both of the fluid to be extracted, i.e. of the fluid mixture, and of the extractant is prevented by the divider. This increases the yield of the extract especially when the internal diameter of the extraction column is relatively high. As described above, it is assumed that, in the process according to the invention too, the divider prevents formation of axial vortices which lead to crossflow of the fluid mixture.

Advantageously in accordance with the invention, at least 25%, better at least 50%, even better at least 75% and preferably the entirety of the stream comprising the constituent to be extracted is extracted in accordance with the invention. The inventive execution of the extraction column achieves depletion levels of up to 99.99% based on the substance to be extracted.

In the process according to the invention, appropriately for application purposes, the phase of higher specific gravity enters the extraction column at the top, and the phase of lower specific gravity at the bottom. In the column, the two phases move in countercurrent.

For example, in the process according to the invention, the fluid to be extracted is first introduced into the column cavity of the extraction column from the bottom. From there, it passes into the regions divided by the divider in the column cavity. The extractant is introduced into the column head at the top. It is added there in droplet form to the regions of the column cavity. The extract mixture is then withdrawn in the column bottom.

Separating internals in particular are disposed in the column cavity of the extraction column. These bring about improved mass transfer between a disperse droplet phase and a continuous phase. The separating internals form liquid droplets, such that the surface area provided by the liquid droplets is constantly newly formed and renewed by splitting and coalescence. The separating internals split the fused droplets back up into smaller droplets, such that the surface area formed by the disperse phase increases again. By means of the separating internals, liquid droplets of the extractant or of the fluid to be extracted are thus formed.

In the process according to the invention, particularly the ratio of the extractant to the fluid to be extracted in the regions is essentially the same over the cross section of the extraction column. The ratio of the extractant to the fluid to be extracted differs over the cross section especially by less than 30%, preferably by less than 10%, more preferably by less than 5%. This configuration of the process gives rise to less axial backmixing in the column and hence also a greater achievable number of plates. In this way, it is thus possible to increase the extraction yields.

In addition, in the process according to the invention, the composition of the extractant and/or the composition of the fluid to be extracted is essentially the same over the cross section of the extraction column, meaning that the distribution of the two phases over the cross section is essentially constant. The difference in the dispersity is, for example, less than 10%, especially less than 5%. This too can increase the extraction yield.

The extractant which is used in the process according to the invention is especially an organic solvent. The fluid to be extracted is especially water comprising acrylic acid and acetic acid, i.e. acid water or acidic water.

Advantageously in accordance with the invention, the extractant will have a higher boiling point than acrylic acid (based in each case on atmospheric pressure), since this generally facilitates the subsequent separation of the acrylic acid from an organic extract.

In the context of the extraction to be conducted in accordance with the invention, the organic solvent to be used as the extractant especially has a significantly higher viscosity than water. In this case, it is advantageous in accordance with the invention when the organic extractant entering the extraction column is present as the disperse phase and the acid water as the continuous phase (this causes, for example, accelerated mass transfer between the two phases and ultimately enables shorter columns with the same separation result; a continuous aqueous phase also gives better wetting of extraction columns manufactured from stainless steel and internals thereof; furthermore, transfer of the substance to be extracted from the continuous phase to the disperse phase leads to stabilization of the latter (lesser tendency to coalescence)). When an organic extractant having a higher mass density than the mass density of the acid water is used, this means that the extractant is applied and dispersed at the top of the column, especially in the form of droplets, and the resulting extractant droplets fall downward in the column. In the reverse case, i.e. when an extractant having a lower mass density than the mass density of acid water is used, the extractant is dispersed in the bottom of the column and the resulting extractant droplets ascend within the column. In the types of extraction columns mentioned so far, having internals in the form of packing elements and/or random packings, the undivided continuous phase should give good wetting of the internals selected, since the droplets of the disperse phase otherwise generally creep along the internals.

In the simplest manner, the organic extractant will be applied by means of tubes (normally having an identical cross section; they are also called tubular distributors) which have generally circular passage orifices (bores), extend over the particular cross-sectional length of the normally circular cylindrical extraction column and are arranged over the column cross section. If the organic extractant is applied at the top of the column, the circular passage orifices point downward; when the extractant is applied at the bottom of the column, they point upward. The diameter (the longitudinal dimension) of the aforementioned passage orifices will typically be 1 mm to 10 mm, preferably 3 mm to 6 mm and in many cases 2 to 5 mm. The extractant is allowed to flow in a simple manner into the distributor tubes and out of the passage orifices again.

The driving force for the separation of extract and raffinate is the difference in the mass density ($g/cm^3$) between the two phases. A high mass density differential in the two liquid phases facilitates the phase separation and reduces emulsion formation.

Advantageously, for the extraction to be conducted in accordance with the invention, therefore, organic solvents having a mass density in $kg/m^3$ differing from the mass density of water (likewise in $kg/m^3$) by $\geq 25$ $kg/m^3$, preferably by $\geq 50$ $kg/m^3$ (based on the pressure employed in the extraction and the temperature employed in the extraction) are used. In general, the aforementioned mass density difference will, however, be $\leq 250$ $kg/m^3$, generally $\leq 150$ $kg/m^3$.

In addition, it is favorable for the process according to the invention when the dynamic viscosity of the organic extractant under the extraction conditions is $\leq 100$ mPa·s, preferably $\leq 50$ mPa·s. In general, the aforementioned dynamic viscosity will, however, be $\geq 1$ mPa·s. Dynamic viscosities particularly favorable in accordance with the invention are in the range from 2 to 10 mPa·s.

In addition, it is advantageous in the process according to the invention when the interfacial tension between the two fluid phases is comparatively high. Against the background of the statements made so far, extractants for the acid water extraction suitable in accordance with the invention include organic liquids whose boiling point at standard pressure (1 atm) is above 150° C. or above 160° C. Examples include middle oil fractions from paraffin distillation, diphenyl ether, diphenyl, or mixtures of the aforementioned liquids, for example a mixture of 70 to 75% by weight of diphenyl ether and 25 to 30% by weight of diphenyl. It is also favorable to use a mixture consisting of a mixture of 70 to 75% by weight of diphenyl ether and 25 to 30% by weight of diphenyl, and also, based on the mixture, 0.1 to 25% by weight of dimethyl o-phthalate.

Organic solvents particularly preferred in accordance with the invention for acid water extraction are the esters of aliphatic or aromatic mono- or dicarboxylic acids (especially when both carboxyl groups have been esterified) wherein the alcoholic component comprises 1 to 8 carbon atoms and the carboxylic acid component 5 to 20 carbon atoms. Preferably, the alcoholic component has merely two hydroxyl groups or only one hydroxyl group prior to the esterification. More preferably, the alcoholic component comprises monohydric (one OH group) or dihydric (two OH groups) alkanols. Advantageously, the number of carbon atoms in the alcoholic component (especially in the case of monohydric or dihydric alkanols) is 1 to 6, more preferably 1 to 4 and most preferably 1 or 2. The aliphatic or aromatic mono- or dicarboxylic acids advantageously comprise 5 to 15 carbon atoms, preferably 5 to 10 carbon atoms and more preferably 6 to 8 carbon atoms (especially in the case of a respective esterification (in the diester case too) with alkanols having 1 to 4 or having 1 or 2 carbon atoms). Dicarboxylic acids are preferred over monocarboxylic acids as the acid component of the relevant esters (especially when both carboxyl groups have been esterified). Phthalic acid, isophthalic acid and terephthalic acid, and also adipic acid, are acid components very particularly preferred in accordance with the invention for the relevant esters. The latter is especially true in the case of the dialkyl esters ($C_1$- to $C_8$-alkyl, advantageously $C_1$- to $C_6$-alkyl, very particularly advantageously $C_1$- to $C_4$-alkyl and even better $C_1$- or $C_2$-alkyl). In other words, extractants very particularly favorable for the process according to the invention are dimethyl phthalate, diethyl phthalate (e.g. Palatinol® A from BASF Aktiengesellschaft), dimethyl isophthalate, diethyl isophthalate, dimethyl terephthalate, diethyl terephthalate, dimethyl adipate and diethyl adipate.

Further esters suitable for the inventive acid water extraction are the triesters of phosphoric acid, for example tributyl phosphate or tricresyl phosphate. Useful cresyl radicals include ortho-cresyl, meta-cresyl and para-cresyl. Other useful extractants for the inventive acid water extraction are esters of acrylic acid and branched or linear monohydric $C_6$- to $C_{12}$-alkanols (e.g. 2-propylheptyl acrylate or 2-ethylhexyl acrylate) and mono- and diesters of maleic acid and monohydric $C_4$- to $C_{10}$-alkanols. Preferred extractants in accordance with the invention are all of those aforementioned extractants which, at standard pressure, have a boiling point above 150° C. or above 160° C., or above 170° C., or above 180° C., or above 190° C.

In general, the acid water to be extracted will comprise, as well as acrylic acid and water, as a further constituent (generally the third-largest constituent in percent by weight based on the total amount of the acid water), acetic acid. According to the manner of the partial oxidation conducted (catalyst selected, steam content of the reaction gas mixture, temperature for the partial oxidation), the acid water may comprise up to 10% by weight, or up to 5% by weight (frequently 2 to 8% by weight) or more, of acetic acid. Frequently, the acid water contains about twice the proportion by weight of acrylic acid, based on the proportion by weight of acetic acid. The contents of the other possible acidic secondary components are normally significantly lower. Preference is therefore given in accordance with the invention to those extractants which preferentially take up the acrylic acid compared to the acetic acid. These extractants include, in particular, diethyl phthalate.

It is also advantageous in accordance with the invention when the extractant does not react with water under the extraction conditions and has only a low solubility in water. For example, diethyl phthalate is particularly hydrolysis-stable. A further advantage of diethyl phthalate is its comparatively high boiling point at standard pressure (1 atm), which, advantageously in accordance with the invention for extractants (organic solvents) to be used, is ≥200° C., better ≥225° C. and even better ≥250° C.

In addition, it has a comparatively low solubility in water (this also reduces the extractant losses). In general, the acid water is obtained in the fractional condensation of the product gas mixture to be performed in accordance with the invention with a temperature of 50 to 80° C., preferably 60 to 70° C. In other words, it is normally withdrawn via the second liquid phase draw (preferably a side draw) at this temperature (the lower the temperature, the lower the requirement for polymerization inhibitor; in favorable cases, there is no need to separately add one to the acid water, extractant, raffinate and/or extract). Appropriately from an application point of view, the extraction will therefore also be performed in this temperature range. In other words, advantageously in accordance with the invention, the acid water will be conducted essentially at its aforementioned temperature into the extraction unit, preferably an extraction column (more preferably a packed column, advantageously Montz-Pak B1-350). Advantageously, it is fed into the extraction column from the bottom, and the extractant of higher specific gravity (advantageously diethyl phthalate) is applied from the top. Typically, the temperature of the extractant applied will not be very different than that of the acid water fed in. Typically, the magnitude of this temperature difference is ≥0° C. and ≤20° C., preferably ≥0° C. and ≤15° C. and in many cases ≥0° C. and ≤10° C. The pressure of the acid water withdrawn from the condensation column is, at the withdrawal point, typically in accordance with the invention >1 to 1.5 bar, frequently 2 bar. The acid water withdrawn is conducted into the extraction column by means of a pump. The delivery pressure may, for example, be 2 to 6 bar. The working pressure in the extraction column is selected in accordance with the invention such that it does not require any additional pump in order to convey the organic extract into the first stripping column. In principle, the acid water extraction can also be performed at higher or lower temperatures and at higher or lower pressures. When an extraction column is put into operation, the procedure will be, appropriately from an application point of view, first to fill the extraction column with acid water and then, as already described, to apply the organic extractant in droplet form, advantageously at the top of the extraction column. The acid water (the preferably continuous phase) can in principle be fed in directly via an appropriate feed nozzle. In principle, the acid water can also be fed in via a feed tube having one (or more) passage orifice(s) in its wall (diameter of the passage orifices is typically from 5 to 10 mm).

The ratio V of the flow rates of organic extractant (E; in kg/h) and acid water (S; in kg/h) fed to the extraction column, i.e. E:S, in the process according to the invention may be 0.05 to 20, preferably 0.1 to 10, better 0.8 to 1.2 and more preferably 1:1.

The acrylic acid-depleted (extracted) acid water is normally sent to its disposal (for example incinerated or conducted into a water treatment plant). Typically in accordance with the invention, it leaves the extraction column at its top (as raffinate), while the organic extract comprising the acrylic acid typically leaves the extraction column at the bottom.

The removal of the acrylic acid from the organic extract, the withdrawal temperature of which from the extraction column corresponds essentially to the feed temperature of the acid water into the extraction column, can in principle be undertaken using different thermal separation processes or else using combinations of such thermal separation processes.

A suitable separation variant is crystallizative separation. Possible crystallization processes include all of those recommended in DE-A 19838845 and in DE-A 10 2005 015 637.

Working examples of the inventive extraction column and working examples of the process according to the invention are elucidated hereinafter with reference to the drawings.

Figure 2:
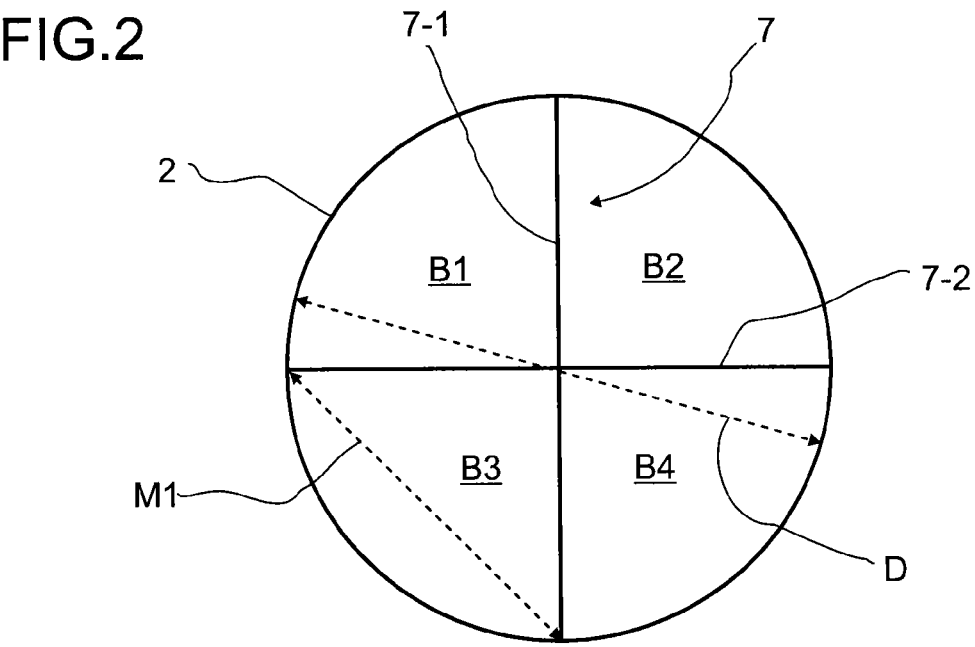
Figure 3:
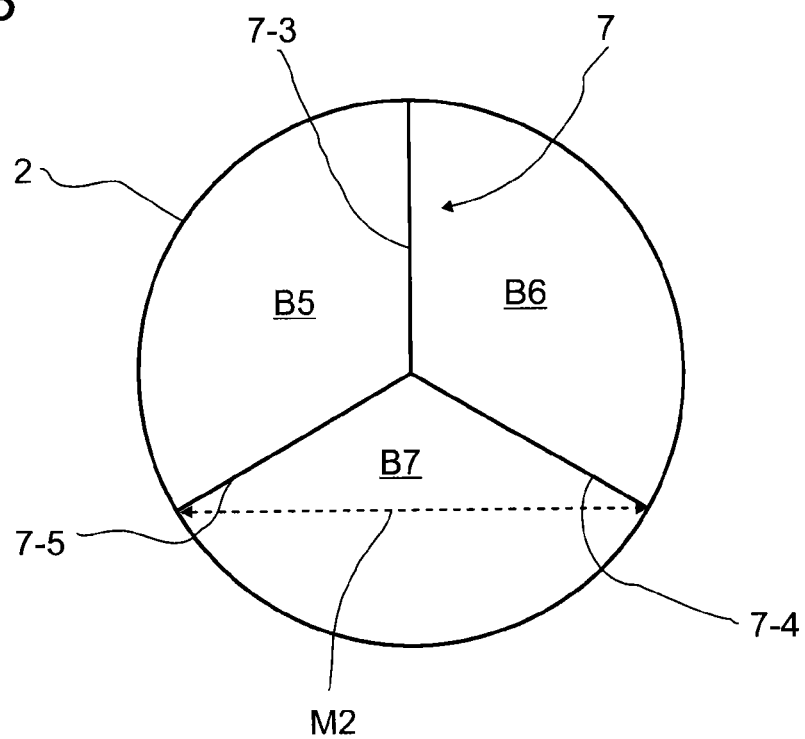
Figure 4:
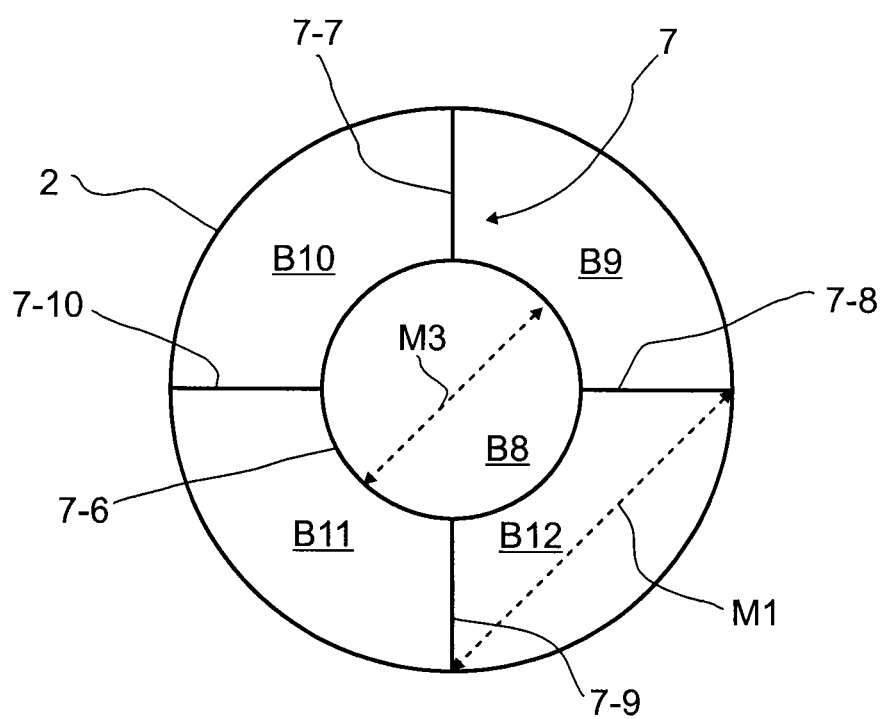
Figure 5:
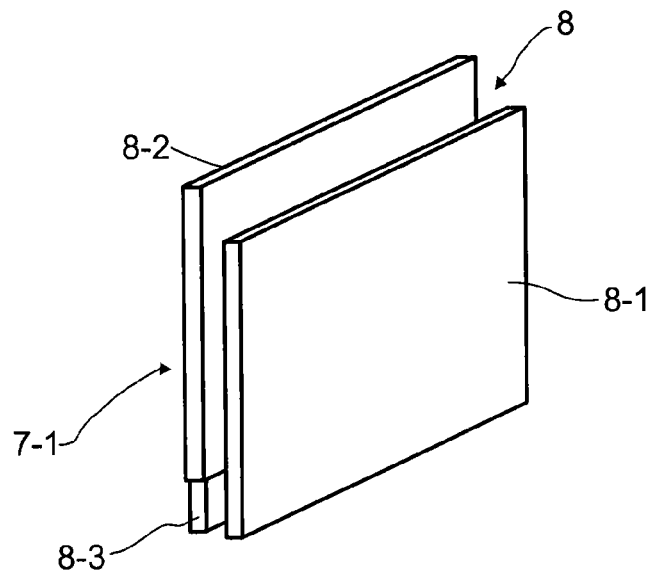
Figure 6:
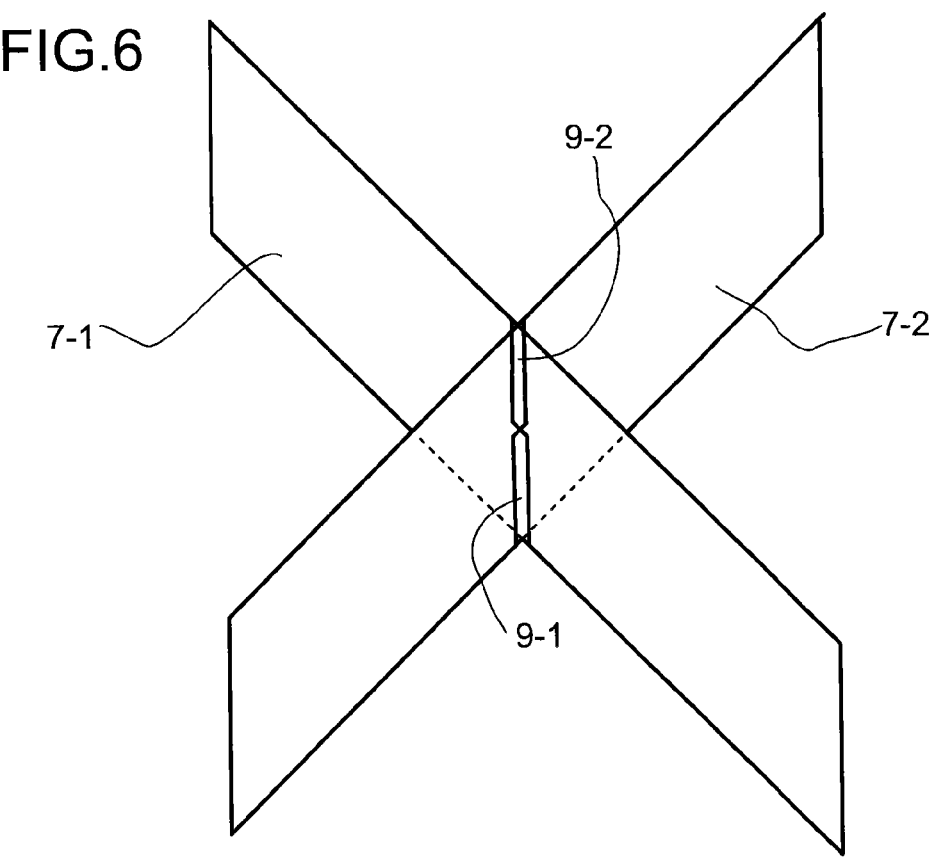
Figure 7:
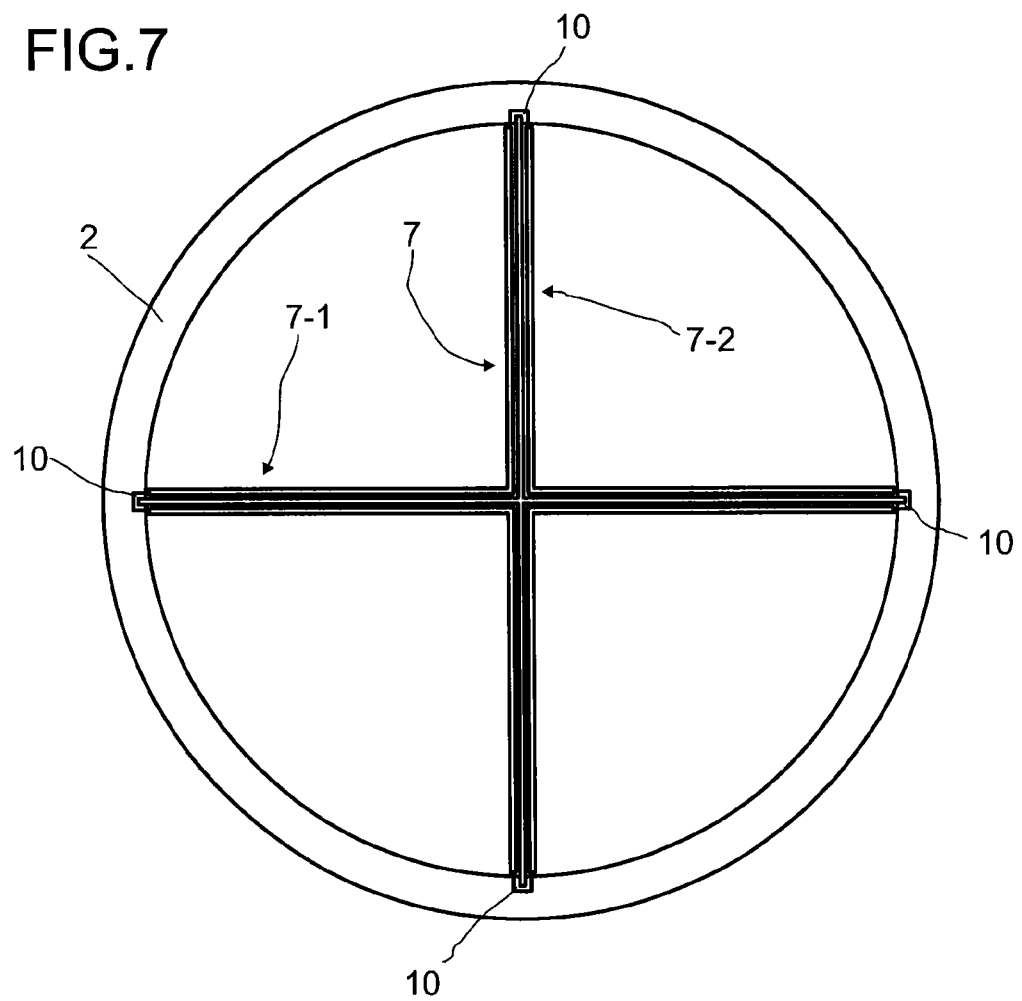
Figure 8:
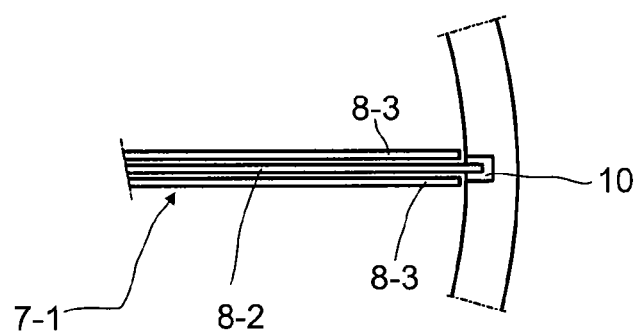
Figure 9:
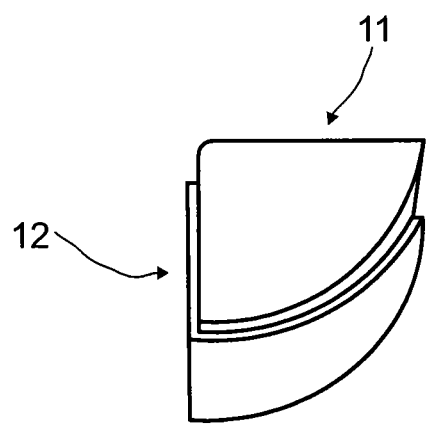
Figure 10:
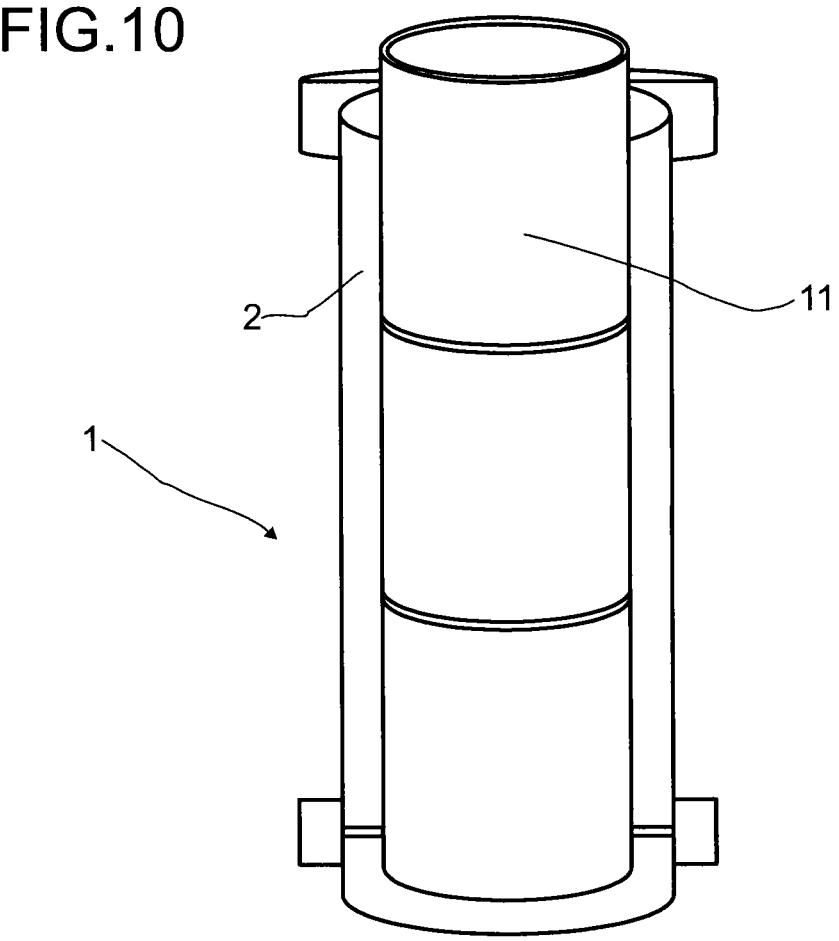

FIG. 1 shows a schematic view of the extraction column in one working example of the invention, FIG. 2 shows a cross section of the extraction column in the working example of the invention, FIG. 3 shows a cross section of an extraction column in another working example of the invention, FIG. 4 shows a cross section of an extraction column in yet a further working example of the invention, FIG. 5 shows part of a dividing sheet of a divider in the working examples of the invention, FIG. 6 shows a divider in the first working example of the invention, FIG. 7 shows the accommodation of the divider of FIG. 6 into a column body in one working example of the invention, FIG. 8 shows the connection of the divider to the column body in detail, FIG. 9 shows an individual packing element for accommodation into the regions of an extraction column in working examples of the invention and FIG. 10 shows a schematic of an extraction column filled with packing elements in working examples of the invention.

The working example described hereinafter relates to the extraction of acrylic acid from acid water by means of an organic solvent. This acid water was withdrawn from a condensation column for preparation of acrylic acid at a side draw. However, it is pointed out that other constituents can also be transferred from a fluid to be extracted, especially an extraction fluid, to an extract mixture by means of an extractant in a corresponding manner.

FIG. 1 shows the extraction column 1 in schematic form. It comprises a cylindrical column body 2, the axis of which is aligned vertically. The column body 2 is essentially a hollow cylinder. This means that the shell of the column body 2 forms a column cavity 3. The column body 2 is manufactured from stainless steel. Typical wall thicknesses are 5 mm to 20 mm. On the outside, the extraction column 1 is normally thermally insulated in a conventional manner. The height of the extraction column 1 is 40 m.

For simpler assembly of the column body 2, it is subdivided into segments 2-1, 2-2, . . . , 2-*n*. In the assembly of the column body 2, the segments 2-1 to 2-*n* are successively placed one on top of another and connected tightly to one another.

In the vertical direction, the extraction column 1 is subdivided into three regions: the upper region is referred to as column head A. In the column head A, a first feed 4 is provided, through which, for example, the extractant can be introduced into the column cavity 3. The first feed 4 is appropriately connected to a tubular distributor through which the extractant can be distributed homogeneously over the cross section of the column body 2.

Also provided at the top of the column A is an outlet 13, through which, for example, the raffinate can be led out of the column cavity 3.

Below the column head A, a region B is formed, in which a divider 7, as will be elucidated in detail later, is arranged within the column cavity 3. Below the region B, the column bottom C is formed. In the column bottom C, there is a second feed 5 through which, for example, the liquid to be extracted, i.e. the acid water in the present case, can be introduced into the column cavity 3. In addition, there is an outlet 6 for the extract mixture in the column bottom C.

FIG. 2 shows the horizontal cross section of the extraction column 1 in the region B in which the divider 7 is arranged. Over the entire region B, the internal diameter D of the column body 2 corresponds to the horizontal maximum extent of the column cavity 3. This horizontal maximum extent refers to the greatest distance between any two points on the inner surface of the column body 2.

Also arranged in the region B of the column cavity 3 is a divider 7. In the example shown in FIG. 2, the divider 7 comprises two dividing sheets 7-1 and 7-2 arranged at right angles to one another. The two dividing sheets 7-1 and 7-2 are joined to one another in the middle of the column cavity 3, i.e. coinciding with the axis of the column body 2, such that they are at right angles to one another. The dividing sheets 7-1 and 7-2 extend horizontally to the inner wall of the column body 2 and conclude tightly at that point. The divider 7 thus subdivides the column cavity 3 into four identical vertically aligned and horizontally divided regions B1, B2, B3 and B4. Within these regions B1 to B4, the lighter phase, i.e. the acid water in the present case, can ascend and the heavier phase, i.e. the extractant in the present case, can descend. In the region B of the extraction column 1, however, mass transfer is impossible between the regions B1 to B4.

It is a feature of the regions B1 to B4 that the horizontal maximum extent M1 of each region D1 to D4 in the region B of the extraction column 1 is less than the horizontal maximum extent D of the column body 2. In the example shown in FIG. 2, the ratio of the horizontal maximum extent M1 of the regions B1 to B4 to the horizontal maximum extent D of the column cavity 3 is equal to $1/\sqrt{2}$, i.e. about 0.7. The divider 7 has thus reduced the horizontal maximum extent within the column body 2 by about 30%.

FIG. 3 shows another example of a divider 7. In this case, the divider 7 consists of three dividing sheets 7-3, 7-4 and 7-5. These are joined to one another in the middle such that they enclose an angle of 120°. From the middle, they extend horizontally to the inner wall of the column body 2. In this way, three vertically aligned and horizontally divided regions B5, B6 and B7 are formed. No mass transfer is possible between these regions B5 to B7.

In the example shown in FIG. 3, the ratio of the horizontal maximum extent M2 of the regions D5 to D7 to the horizontal maximum extent D of the column cavity 3 is equal to cos 30°, i.e. about 0.86. In this case too, the horizontal maximum extent of the column cavity 3 is thus significantly reduced.

It is also a feature of the regions B1 to B4 of the example according to FIG. 2 and the regions B5 to B7 of the example according to FIG. 3 that the regions each have identical geometry and enclose the same volume. This ensures that the same conditions for the extraction will exist within each of the regions B1 to B4 or of the regions B5 to B7.

FIG. 4 shows a further example of a divider 7 arranged in the region B of the extraction column 1. In this case, the divider 7 comprises a dividing sheet 7-6 which is circular in cross section and is arranged concentrically with respect to the column body 2. In this way, the dividing sheet 7-6 delimits a vertically aligned circular cylindrical region B8. The diameter of the circle, i.e. the horizontal maximum extent M3 of the region B8, is smaller than the horizontal maximum extent D of the column cavity 3.

From the outside of the dividing sheet 7-6, four further dividing sheets 7-7 to 7-10 extend radially outwards to the inner wall of the column body 2. The dividing sheets 7-7 and 7-9 are arranged on opposite sides of the dividing sheet 7-6. The dividing sheets 7-8 and 7-10 are likewise arranged on opposite sides of the dividing sheet 7-6. The dividing sheets 7-7 and 7-9 are arranged on a first theoretical straight line; the dividing sheets 7-8 and 7-10 are arranged on a second theoretical straight line. The first theoretical straight line is at right angles to the second theoretical straight line. The dividing sheets 7-7 to 7-10 and the dividing sheet 7-6, and also the column body 2, delimit four further regions B9, B10, B11 and B12.

The cross-sectional area of the regions B9 to B12 is identical. It differs, however, from the disk-shaped cross-sectional area of the region B8. The diameter M3 of the region B8 is, however, selected such that the cross-sectional areas of the regions B8 to B12 are equal, so that the regions B8 to B12 encompass the same volumes. This means that the ratio of the diameter D of the column cavity to the diameter M3 of the region D8 is equal to $\sqrt{5}$.

With reference to FIG. 5, the formation of the dividing sheet 7-1 is described in detail. All the other dividing sheets 7-2 to 7-5 and 7-7 to 7-10, which extend to the inner wall of the shell of the column body 2, may be constructed correspondingly. The dividing sheet 7-1 shown in a section in FIG. 5 consists of several layers 8. FIG. 5 shows a three-layer structure composed of layers 8-1, 8-2 and 8-3. The layers are joined to one another over the full area, with the middle layer 8-2 protruding at the top and at the sides where the dividing sheet 7-1 adjoins the inner wall of the column body 2. In the lower region of the dividing sheet 7-1, a groove is correspondingly formed in the middle, such that a plurality of dividing sheets 7-1 can be placed one on top of another, with the middle layer 8-2 protruding at the side in each case.

As shown in FIG. 6, the dividing sheets 7-1 and 7-2 which are joined to give the divider 7 shown in FIG. 2 have slots 9-1 and 9-2 in the middle. The slot 9-1 in the dividing sheet 7-1 runs from the bottom upward, and the slot 9-2 in the dividing sheet 7-2 runs from the top downward, such that the dividing sheets 7-1 and 7-2 can be inserted into one another in a crosswise manner. The assembled dividing sheets 7-1 and 7-2, as shown in FIG. 6, form a vertical segment of the divider 7. A plurality of vertical segments placed one on top of another give rise to the full divider 7, as shown in FIG. 2.

With reference to FIGS. 7 and 8, the coupling of the divider 7 to the inner wall of the column body 2 is elucidated. For the accommodation of the divider 7 in the inner wall of the column body 2 with prevention of rotation, grooves 10 are formed in this inner wall. Each of the grooves 10 is arranged at the position on the inner wall of the column body 2 at which the divider 7 tightly concludes a region. The dimensions of the dividing sheets 7-1 and 7-2 are such that the transverse extent of the layers 8-1 and 8-3 corresponds essentially to the internal diameter D of the column body 2. The middle layer 8-2 protrudes such that it exactly engages in the grooves 10. This is shown schematically in FIGS. 7 and 8. In the ideal case, the regions B1 to B4 are sealed by the connection of the end faces of the layers 8-1 to 8-2 of the dividing sheets 7-1 and 7-2 to the inner wall of the column body 2, and of the end face of the layer 8-3 in the corresponding groove 10. The dividing sheets 7-1 and 7-2 inserted into one another can be inserted in this way from above into a segment 2-1 to 2-n of the column body 2.

The regions of the column cavity isolated by the divider 7 are filled by separating internals. In the present working example, the internals used were structured packing elements of the B1-350 flat and holed design from Montz or the same SMV 350 design from Sulzer.

The geometry of the packing elements corresponds to the geometry of the regions isolated by the divider 7. In vertical direction, however, the packing elements are subdivided. A plurality of identical individual packing elements are placed one on top of another.

FIG. 9 shows an individual packing element 11 of this kind. It is configured for the divider 7 shown in FIG. 2. The cross-sectional area of this individual packing element 11 corresponds exactly to the cross-sectional area of the regions B1 to B4. For all the regions B1 to B4, it is thus possible to use the same individual packing elements 11. In order to balance out tolerances in the production of the individual packing elements 11, a metal fabric tape 12 is wound around the individual packing element 11.

The extraction column 1 is thus assembled as follows:

First of all, part of the column body 2 is built. For this purpose, the lowermost segment 2-1 of the column body 2 can be set up. Optionally, it is also possible to assemble several segments 2-1 to 2-m one on top of another up to a particular height. This height is selected such that an assembly fitter can safely lower dividing sheets 7-1 and 7-2 and packing elements 11 from the top downward to an assembly fitter at the base of the part of the column body 2. Any risk that falling parts could seriously injure an assembly fitter at the base of the column body 2 should be avoided. For example, the column body 2 is at first built up to a height of 10 m.

The lowermost segment 2-1 comprises the second feed 5 and the outlet 6, and also optionally tubular distributors within the column body 2. If a packing element is to be arranged in the column bottom C of the column body 2, this packing element is at first assembled in the column bottom C. The arrangement of a packing element in the column bottom is optional. A packing element used here could be a random packing element, such as the DN25 Pall rings.

Subsequently, a vertical segment of the divider 7 is inserted. For this purpose, the segments of the column body 2 have grooves 10 in the region B, as shown in FIGS. 7 and 8.

The dividing sheets 7-1 and 7-2 of a divider 7 are lowered down to an assembly fitter standing at the base of the column body 2. This assembly fitter assembles them crosswise, as shown in FIG. 6, and secures the dividers 7 in the grooves 10 of the column body 2. Thereafter, four individual packing elements 11, as shown in FIG. 9, are lowered down to the assembly fitter. The assembly fitter inserts these individual packing elements 11 into the four regions which have been formed by the divider 7. Subsequently, further dividing sheets 7-1 and 7-2 are lowered down to the assembly fitter, and he assembles them crosswise and places them on the already assembled divider 7 such that the part of the layer 8-2 of the already assembled divider 7 which protrudes at the top engages in the lower groove of the divider 7 to be assembled. In addition, the parts of the middle layer 8-2 which protrude on the outside also engage in the grooves 10. Subsequently, four individual packing elements 11 are again placed onto the individual packing elements 11 below. In this way, the assembled part of the column body 2 is subsequently filled with vertical segments of the divider 7 and with individual packing elements 11.

On reaching the upper end of the part of the column body 2, a further part of the column body 2 is assembled by means of the individual segments. Subsequently, in the same way, further vertical segments of the divider 7 and individual packing elements 11 are assembled in the column body 2 growing upward, until the column body 2 has been fully constructed. At the column head A, no further dividers 7 are assembled. As in the column bottom C, however, packing elements which extend over the entire internal diameter of the shell of the column body are used. FIG. 10 shows the fully constructed column body 2 of the extraction column 1. The uppermost packing segment can project somewhat, for example by 10 cm, beyond the column body 2. In the region of the column head A, it is also possible for appropriate tubular distributors coupled to the first feed 4 to be assembled, in order to distribute the extractant homogeneously over the cross-sectional area of the column cavity 3 and to charge the divided regions B1 to B4 and B5 to B7 and B8 to B12 beneath.

A working example of the process according to the invention which is executed with the extraction column 1 described above is described hereinafter.

Via the second feed 5, the acid water to be extracted is fed into the extraction column 1 below the lowermost packing element 11 through a tubular distributor having appropriate passage orifices.

The acid water without added inhibitor has, for example, the following contents:
2.36% by weight of formaldehyde,
83.12% by weight of water,
3.98% by weight of acetic acid,
9.70% by weight of acrylic acid,
0.68% by weight of formic acid, and
0.01% by weight of diacrylic acid.

The specific mass of the acid water is 967.5 kg/m$^3$.

Subsequently, above the uppermost packing element, the extractant is applied via the first feed 4 and a tubular distributor having appropriate passage orifices (holes of diameter 4 mm).

The extractant has, for example, the following contents:
≤0.5% by weight of acrylic acid,
≤0.03% by weight of acetic acid,
≤0.02% by weight of water,
≤0.001% by weight of formic acid,
≤0.0035% by weight of acrolein,
≤0.0005% by weight of propionic acid,
≤0.0001% by weight of furfurals,
≤0.001% by weight of allyl formate,
0.03% by weight of MEHQ,
0.0001% by weight of oxygen, and
≥99.5% by weight of Palatinol® A.

The specific mass of the extractant is 1120 kg/m$^3$.

The extract mixture has an elevated proportion of acrylic acid compared to the extractant, and the raffinate has a reduced proportion of acrylic acid compared to the acid water.

The acid water forms the continuous phase and the extractant forms the disperse phase distributed in droplet form (droplet diameter within the range from 2 to 5 mm), which descends in the aqueous phase.

At the top A of the extraction column 1, the raffinate is withdrawn. It has a reduced content of acrylic acid compared to the acid water. It is sent to incineration together with residual gas for incineration.

The extract mixture is withdrawn from the bottom C of the extraction column 1. It has an elevated content of acrylic acid compared to the extractant.

LIST OF REFERENCE NUMERALS 1 extraction column
2 column body
2-1 to 2-$n$ segments of the column body
3 column cavity
4 first feed
5 second feed
6 outlet
7 divider
7-1 to 7-10 dividing sheets
8, 8-1 to 8-3 layers
9, 9-1, 9-2 slots
10 grooves
11 packing element; individual packing element
12 metal fabric tape
13 outlet

The invention claimed is:

1. An extraction column having
a vertically aligned column body which is cylindrical at least in sections and forms a column cavity having a horizontal maximum extent, wherein the column body comprises a first feed configured for an extractant, a second feed configured for the fluid to be extracted and a first outlet configured for the extract mixture and a second outlet configured for the raffinate,
and wherein
a vertically aligned divider arranged within the column cavity subdivides the column cavity into a plurality of vertically aligned and horizontally divided regions, a horizontal maximum extent of each region being less than a horizontal maximum extent of the column cavity, and
the horizontal maximum extent of the column cavity is greater than or equal to 800 mm.

2. The extraction column according to claim 1, wherein the horizontal maximum extent of each region at each horizontal section through the column body cut by the divider is less than the horizontal maximum extent of the column cavity.

3. The extraction column according to claim 1, wherein the column body is circular at a horizontal section through the column body, and the divider subdivides the column cavity into four vertically aligned and horizontally divided regions.

4. The extraction column according to claim 1, wherein the regions formed by the divider are of equal size.

5. The extraction column according to claim 1, wherein, at each horizontal section through the column body cut by the divider, the regions formed by the divider have the same geometry.

6. The extraction column according to claim 1, wherein the horizontal maximum extent of the column cavity is greater than or equal to 1000 mm.

7. The extraction column according to claim 1, wherein separating internals are arranged within the column cavity.

8. The extraction column according to claim 7, wherein the separating internals for the regions formed by the divider are separate from one another.

9. The extraction column according to claim 7, wherein the separating internals are configured such that they form liquid droplets.

10. The extraction column according to claim 1, wherein the divider is subdivided into vertical segments placed one on top of another in the column cavity.

11. The extraction column according to claim 7, wherein the separating internals in the regions formed by the divider are formed from identical individual packing elements.

12. The extraction column according to claim 1, wherein a vertically aligned groove in which the divider engages is formed on the inside of the column body.

13. The extraction column according to claim 12, wherein the divider comprises at least three layers, and the middle layer protrudes with respect to the outer layers and engages in the groove.

14. A process for extracting a constituent from a fluid by means of an extraction column according to claim 1, the process comprising
introducing the fluid to be extracted into a plurality of vertically aligned and horizontally divided regions which are formed in the column cavity by a vertically aligned divider which subdivides the column cavity into the regions, a horizontal maximum extent of each region being less than the horizontal maximum extent of the column cavity;
introducing an extractant into the regions of the column cavity; and
absorbing the constituent of the fluid to be extracted with the extractant in the regions of the column cavity and withdrawing it as an extract mixture.

15. The process according to claim 14, wherein a ratio of the extractant to the fluid to be extracted in the regions is essentially equal over a cross section of the extraction column.

16. The process according to claim 14, wherein liquid droplets of the extractant or of the fluid to be extracted are formed by means of separating internals in the column cavity.

17. The process according to claim 14, wherein the composition of the extractant and/or the composition of the fluid to be extracted in the regions is essentially equal over a cross section of the extraction column.

18. The process according to claim 14, wherein the extractant is an organic solvent and the fluid to be extracted is water comprising acrylic acid and acetic acid.

19. An extraction column having
a vertically aligned column body which is cylindrical at least in sections and forms a column cavity having a horizontal maximum extent, wherein the column body comprises a first feed configured for an extractant, a second feed configured for the fluid to be extracted and a first outlet configured for the extract mixture and a second outlet configured for the raffinate,
and wherein
a vertically aligned divider arranged within the column cavity subdivides the column cavity into a plurality of vertically aligned and horizontally divided regions, a horizontal cavity, and
wherein the column body is circular at a horizontal section through the column body, and the divider subdivides the column cavity into four vertically aligned and horizontally divided regions.

20. An extraction column having
a vertically aligned column body which is cylindrical at least in sections and forms a column cavity having a horizontal maximum extent, wherein the column body comprises a first feed configured for an extractant, a second feed configured for the fluid to be extracted and a first outlet configured for the extract mixture and a second outlet configured for the raffinate,
and wherein
a vertically aligned divider arranged within the column cavity subdivides the column cavity into a plurality of vertically aligned and horizontally divided regions, a horizontal maximum extent of each region being less than a horizontal maximum extent of the column cavity, and
separating internals are arranged within the column cavity.

21. The extraction column according to claim 20, wherein the separating internals for the regions formed by the divider are separate from one another.

22. The extraction column according to claim 20, wherein the separating internals are configured such that they form liquid droplets.

23. The extraction column according to claim 20, wherein the divider is subdivided into vertical segments placed one on top of another in the column cavity.

24. The extraction column according to claim 20, wherein the separating internals in the regions formed by the divider are formed from identical individual packing elements.

25. An extraction column having
a vertically aligned column body which is cylindrical at least in sections and forms a column cavity having a horizontal maximum extent, wherein the column body comprises a first feed configured for an extractant, a second feed configured for the fluid to be extracted and a first outlet configured for the extract mixture and a second outlet configured for the raffinate,
and wherein
a vertically aligned divider arranged within the column cavity subdivides the column cavity into a plurality of vertically aligned and horizontally divided regions, a horizontal maximum extent of each region being less than a horizontal maximum extent of the column cavity, and
a vertically aligned groove in which the divider engages is formed on the inside of the column body.

26. The extraction column according to claim 25, wherein the divider comprises at least three layers, and the middle layer protrudes with respect to the outer layers and engages in the groove.

* * * * *